United States Patent [19]

Kobel et al.

[11] Patent Number: 4,542,135

[45] Date of Patent: Sep. 17, 1985

[54] 9'THIA-ERGOTS

[75] Inventors: Hans Kobel, Basel; Jean-Jacques Sanglier, Oberwil; Hans Tscherter, Allschwil; Georg Bolliger, Binningen, all of Switzerland

[73] Assignee: Sandoz Ltd., Basel, Switzerland

[21] Appl. No.: 404,832

[22] Filed: Aug. 3, 1982

[30] Foreign Application Priority Data

Aug. 7, 1981 [CH] Switzerland ..................... 5104/81

[51] Int. Cl.$^4$ .................... C07D 519/02; A61K 31/48
[52] U.S. Cl. ..................................... 514/250; 544/346; 546/69
[58] Field of Search ......................... 544/346; 424/261

[56] References Cited

FOREIGN PATENT DOCUMENTS

| 2803543 | 8/1979 | Fed. Rep. of Germany ...... 424/261 |
| 602766 | 7/1978 | Switzerland ......................... 424/261 |
| 636011 | 5/1983 | Switzerland ......................... 424/261 |
| 2030567 | 4/1980 | United Kingdom ................ 424/261 |

OTHER PUBLICATIONS

Baumert et al., "Incorporation of Thiazolidine-4-Carboxylic Acid into Erosine...," *Chem. Abst.* 96: 213910r (1982).

*Primary Examiner*—Donald G. Daus
*Assistant Examiner*—G. Hendricks
*Attorney, Agent, or Firm*—Gerald D. Sharkin; Robert S. Honor; Thomas O. McGovern

[57] ABSTRACT

9-Thia ergot cyclic peptide alkaloids produced by fermentation or synthetic methods have interesting antiparkinson and other pharmacological activities.

15 Claims, No Drawings

9'THIA-ERGOTS

This invention relates to ergot cyclic peptide alkaloids, their production and pharmaceutical compositions containing them.

Such ergot cyclic peptide alkaloids contain an optionally substituted ergoline nucleus linked at the 8-position thereof to a tricyclic peptide moiety commonly referred to as an amino-cyclol, e.g. 2-amino-octahydro-10b-hydroxy-3,6-dioxo-8H-oxazolo[3,2-a]pyrrolo[2,1-c]pyrazine and analogues thereof.

Such ergot alkaloids may be obtainable from natural sources, e.g. by fermentation, and by chemical synthetic methods, or be obtainable only by chemical synthetic methods.

The present invention provides in one aspect 9'-thia-ergot cyclic peptide alkaloids, herein referred to as compounds of the invention.

The methylene group in the 9 position of the aminocyclol is accordingly replaced by sulphur. Such ergot cyclic peptide alkaloids may exist in isomeric form. For example in the 8 position of the ergoline nucleus the carbon atom may have the R or S configuration.

In particular the present invention provides a compound of formula I

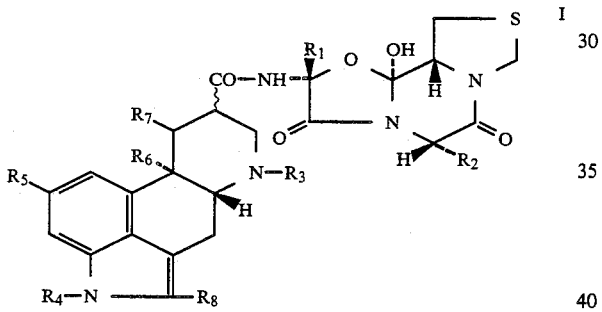

wherein
$R_1$ is $(C_{1-4})$alkyl,
$R_2$ is $(C_{1-6})$alkyl or benzyl,
$R_3$ and $R_4$ independently are hydrogen or $(C_{1-4})$alkyl,
$R_5$ is hydrogen or bromine,
$R_6$ and $R_7$ are each hydrogen, or
$R_6$ and $R_7$ together form a single bond, or
$R_6$ is methoxy and $R_7$ is hydrogen, and
$R_8$ is hydrogen, methyl, or halogen of atomic number from 9 to 35.
with the proviso that when $R_5$ is bromine, then $R_7$ is hydrogen.

In formula I $R_1$ is for example methyl or isopropyl. $R_2$ is for example n- or iso-propyl, n-, iso- or sec-butyl, or benzyl. $R_3$ is for example n- or iso-propyl or preferably ethyl or methyl. $R_4$ is preferably hydrogen or methyl. $R_5$ is preferably hydrogen. $R_6$ and $R_7$ conveniently form a single bond or are each hydrogen. $R_8$ is conveniently hydrogen, bromine or methyl.

As indicated above the compounds of formula I may exist in isomeric form, e.g. the 8R and 8S isomers. The 8R isomers are preferred.

In accordance with the present invention a compound of the invention may be produced by a process characterised by (a) condensing an acid addition salt of an appropriate 9-thia-aminocyclol or a precursor thereof with an reactive acid derivative of an appropriate lysergic acid derivative or a precursor thereof, or (b) for the production of a 9'-thia analogue of a ergot cyclic peptide alkaloid having a 9'-methylene group and obtainable by fermentation, cultivating a strain capable of producing the 9'-methylene ergot cyclic peptide alkaloid in the presence of L-thiazolidine-4-carboxylic acid or a precursor thereof.

The 9'-thia ergot cyclic peptide alkaloid may be recovered e.g. in free base form or in acid addition salt form.

In particular a compound of formula I as defined above may be produced by a process characterised by (a) condensing an acid addition salt of a compound of formula II

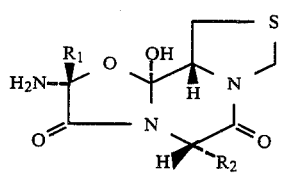

wherein $R_1$ and $R_2$ are as defined above, or a precursor thereof, with a reactive acid derivative of a compound of formula III

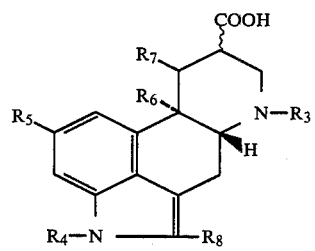

wherein $R_3, R_4, R_5, R_6, R_7$ andh $R_8$ are as defined above, or a precursor thereof, or (b) for the production of a compound of formula Ia

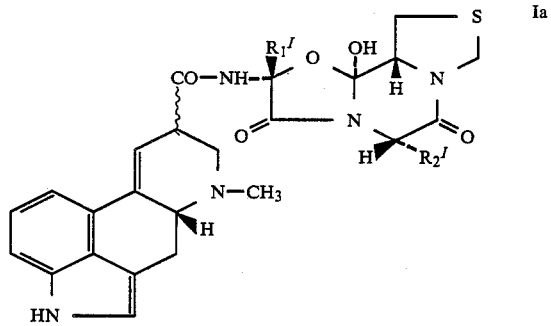

wherein
$R_1^I$ is methyl and $R_2^I$ is isobutyl or benzyl, or
$R_1^I$ is ethyl and $R_2^I$ is benzyl, or
$R_1^I$ is isopropyl and $R_2^I$ is isopropyl, sec-butyl, isobutyl, or benzyl,
cultivating a strain capable of producing the corresponding ergot alkaloid having a 9'-methylene group in the presence of L-thiazolidine-4-carboxylic acid or a precursor thereof.

The compound of formula I or Ia may be recovered, e.g. in free base form or in acid addition salt form.

As indicated above a precursor of a particular starting material may be used. Such a precursor may be a compound which is capable of being converted into the starting material using conventional reactions. After the above defined step (a) or (b) is effected then the product may be converted into a compound of the invention, e.g. using the conventional reactions. For example an amino group may be temporarily protected.

Process (a) may be effected in conventional manner for the production of ergot cyclic peptide alkaloids by condensing appropriate aminocyclols with appropriate lysergic acid derivatives.

Conveniently the aminocyclol is in the form of the hydrochloride.

The lysergic acid derivative is conveniently the acid chloride, acid azide, or a mixed anhydride with sulphuric acid or trifluoroacetic acid. Preferably the lysergic acid derivative is an addition product with dimethylformamide or acetamide, and thionyl chloride, phosgene, or oxalyl chloride. Preferably the reaction is effected in the presence of triethylamine or pyridine. Suitable solvents are for example chloroform, methylene chloride, dimethylformamide, or acetonitrile.

Suitable reaction temperatures are from about $-30°$ to about $+20°$ C.

The 9-thia-aminocyclol compounds used as starting materials are new and also form part of the invention.

The preferred 9-thia-aminocyclols are those of formula II as defined above.

The compounds of formula II may be produced in conventional manner as described in the following flowsheet wherein Y is a protecting group, e.g. ethoxy, and Z is a protecting group, e.g. benzyloxycarbonyl. Other 9-thia-aminocyclols may be produced in analogous manner.

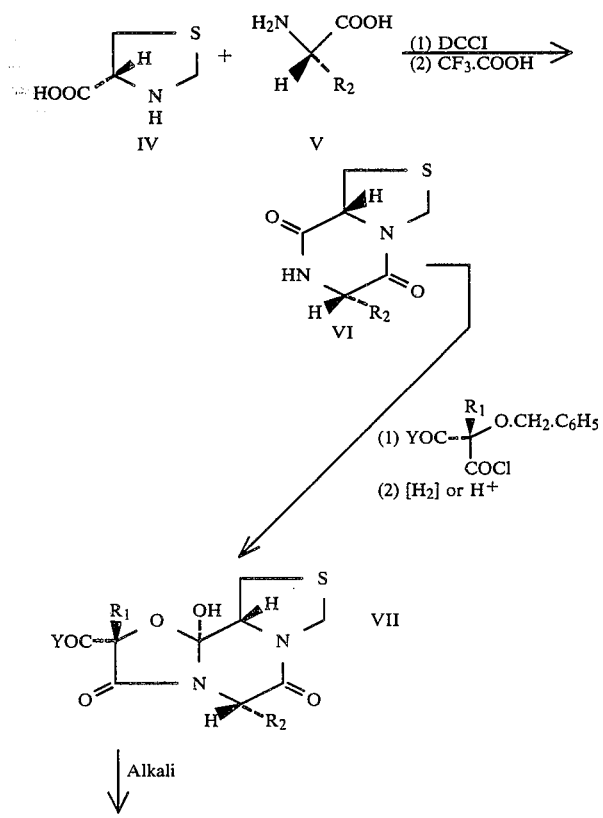

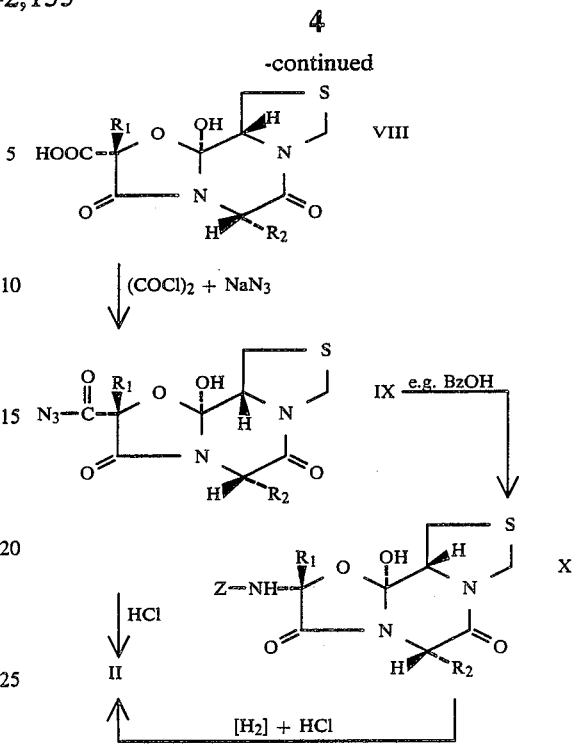

The compounds VI, VII, VIII, IX and X are new and each per se forms part of the present invention.

The lysergic acid derivatives are in general known.

Process (a) is the preferred process for the production of the compounds of the invention.

Process (b) may be effected in conventional manner for the production of ergot cyclic peptide alkaloids by cultivation of microorganisms.

The strains used for cultivation may be strains used for the production of the corresponding ergot cyclic peptide alkaloids having a methylene group in the 9'-position, preferably ergotamine and ergocristine. Such strains may be strains of Claviceps purpurea. The strains may be isolated from nature or produced from other Claviceps purpurea strains which are treated with radiation or mutagenic substances, or produced by selection from other strains.

For the production of 9'-thia-ergotamine and 9'-thia-ergotaminine the preferred strain is the ergotamine/ergotaminine-producing strain of Claviceps purpurea deposited on Sept. 20, 1979 at the United States Department of Agriculture (Northern Regional Research Laboratory), Peoria, Ill., under the number NRRL 12043. For the production of 9'-thia-ergocristine and 9'-thiaergocristinine the preferred strain is the ergocristine/ergocristinine producing strain of Claviceps purpurea deposited on Sept. 20, 1979 at the United States Department of Agriculture Peoria, Ill., unter the number NRRL 12044.

These strains are new and form part of the present invention.

The strains NRRL 12043 and 12044 are freely available from the above-mentioned depository and also from the patentee.

Suitable strains used for the production of other ergot cyclic peptide alkaloids are known and are freely available from established sources.

Characterisation and fermentation of strains NRRL 12043 and NRRL 12044

(a) Characterisation of the strain NRRL 12043

The strain used as starting material was isolated from an ergotamine containing sclerotium obtained from Bromus, Valais, Switzerland and was subjected to several mutation steps using ultra-violet radiation and mutagenic chemicals to produce NRRL 12043.

A small mycelium piece of the strain is inoculated in the centre of an Agar plate of a sterilized medium. This has the following composition: 60 g saccharose, 10 g asparagine, 0.5 g casein amino acids (known under the brand Difco), 0.25 g $KH_2PO_4$, 0.25 g $MgSO_4.7H_2O$, 0.125 g KCl, 16 mg $FeSO_4.7H_2O$, 10 mg $ZnSO_4.7H_2O$, 15 g Agar and distilled water to 1 liter. The pH is adjusted to 6.0 with 25% ammonium hydroxide. The medium is sterilized at 120° C. for 20 minutes.

After 7 days at 24° C. a colony of about 3 cm in diameter is produced. After 14 days the diameter is about 5 cm and after 14 days about 8 cm. The colony is elevated and slightly wrinkled. The edge is diffuse. The colour of of the colony is beige-violet in the centre and at the edge grey-beige. A 20 day old colony contains per $cm^2$ habout $1 \times 10^8$ conidia. The conidia are oval. Their dimensions about $6-12 \times 4-7$ microns.

(b) Characterisation of the strain NRRL 12044

The strain used as starting material was isolated from an ergocristine containing sclerotium obtained from rye in N. America and was subjected to several mutation steps using ultra-violet radiation and mutagenic chemicals to produce NRRL 12044.

A small mycelium piece of the strain is inoculated in the centre of an Agar plate of a sterilized medium. This has the following composition: 70 g malt extract (obtained from Wander, Switzerland), 30 g potato extract (Brand Stöckli, obtained from Knorr), 15 g Agar and distilled water to 1 liter. The pH value is from 5.3 to 5.7. The medium is sterilized at 120° C. for 20 minutes.

After 7 days at 24° C. a colony of about 2 cm in diameter is produced. After 14 days the diameter is about 4 cm and after 20 days about 5 cm.

The mycelium is smoothly elevated and covered with white wool-like hyphae, with a plaited structure which towers about it. In the centre there is a crater-forming hump about 1 cm diameter from which radial plaits extend. The mycelium lying on the agar is coloured violet, and comprise concentric alternating zones, some strongly coloured and others less strongly coloured, the edge being diffuse. A 20 day old colony contains per $cm^2$ about $1 \times 10^8$ conidia. These vary a lot in their dimensions, $5-12 \times 3-7$ microns, but mostly are $5-6 \times 3$ microns.

The mycelium contains no alkaloids.

Cultivation and inoculation (a) NRRL 12043

Cultivation and inoculation of the strain NRRL 12043 may be effected by washing the conidia from one of the above described colonies in sterile water and then inoculating for example an agar sterilized medium in a agar-slant. This comprises 70 g malt extract (brand Wander, Switzerland), 30 g potato extract (brand Stöckli, Knorr, Switzerland), 15 g Agar and distilled water to 1 liter. The pH value may be from 5.3 to 5.7. The medium may be sterilized for 20 minutes at 120° C. After 14 days such a agar-slant culture containing 12 ml medium in a glass tube of 18 mm diameter and 20 cm in length has about $1.10^9$ conidia. The conidia from such a agar slant are washed in sterile water to produce a concentration of about $10^6$–$10^7$ conidia per ml. 0.5 ml of this suspension is used to inoculate agar slants having the same agar medium. These cultures are cultivated at 24° C. for 14 days and then stored at −40° C.

(b) NRRL 12044

Cultivation and inoculation of the strain NRRL 12044 may be effected by washing the conidia from one of the above described colonies in sterile water and then inoculating for example the above defined agar medium for NRRL 12044. After 18 days such a agar slant culture grown as for NRRL 12043 contains about $1-2.10^9$ conidia. These conidia are further cultivated as for NRRL 12043.

Pre-culture

Preferably a preculture of the strain is made before the fermentation culture, using a medium which allows good spore cultivation and a quick mycelial growth. Suitable media may be concentrated carbon sources in the form of a mono- or di-saccharide, optionally in combination with a polyalcohol, a nitrogen source in the form of an amino acid or an ammonium salt, mineral salts, trace elements and plant additives.

Preferably the pH is from 5 to 7. Firstly the medium may be adequately inoculated with conidia and incubated in shaker machines or fermenters at about 22° to 26° C. for 4 to 7 days. A thick culture results of loose, wool-like unpigmented mycelial pieces sized about 2 to 3 mm which have long hyphae of about 2 to 6 microns in diameter.

Fermentation culture

The fermentation culture may be inoculated with part of the pre-culture, or the last of a series of pre-cultures, in a nutrient medium which preferably has a composition which provides in a short time a high mycelium mass.

Suitable carbon sources include saccharose; suitable nitrogen sources include ammonium salts such as the oxalate, citrate, succinate or formate. Mineral salts and trace elements such as iron and zinc should be present. The cultures may be cultivated in Erlenmeyer flasks or fermenters. An adequate air supply should be present. The preferred temperature is 24° C.

At the start of the alkaloid formation, generally between the 3rd and 6th day of the fermentation the sulphur source may be added, e.g. L-thiazolidine-4-carboxylic acid in free form or in protected form or in salt form e.g. the potassium, sodium or ammonium salt. The preferred concentration of this compound is about 1 to 5 g/liter culture.

The culture is preferably cultivated for a further 6 to 12 days. Within 9 to 18 days a thick culture which mainly comprises besides fine mycelial pieces mainly compact cylindrical mycelial pieces which are about 0.5 to 3 mm long and about 0.1 to 1 mm thick.

The mycelial pieces appear like plectenchymic tissue of spherical or polyhedric to short-cylindrical, thick walled and strongly vacuolated cells of $6-12 \times 6-14$ microns, mainly $8 \times 9$ microns, which are traversed by up to 100 micron long hyphae. They have a brown pigment. The culture filtrate is also coloured brown.

When the increase in weight and in the alkaloid content of the mycelium lessens the alkaloids may be extracted in conventional manner with organic solvents from the whole culture broth. Alternatively the mycelium may be separated by filtration or centrifugation and the mycelium and the non-mycelium part separately extracted. The ergot alkaloids exist mostly in the mycelium.

Isolation of 9'-thia ergot cyclic peptide alkaloids

These alkaloids may be isolated from the culture broth, the culture filtrate or the mycelium using conventional extraction methods. The purification may be effected using known purification methods, e.g. using different solvents or converting the substances into difficultly soluble salts. Preferably purification is effected by chromatography, e.g. on aluminium oxide, silicagel, sephadex etc using appropriate solvent systems. Preferably the isolation is effected in the dark, and minimizing formation of the free base form and the use of polar solvents in order to minimize decomposition or isomerisation.

In another aspect the invention provides a biologically pure or axenic Claviceps purpurea culture having the identifying characteristics of the strain deposited under the accession number NRRL 12043 or 12044.

In a further aspect the invention provides a culture medium containing a strain or culture as defined above.

If desired the compounds of the present invention may be converted into other compounds of the invention e.g. using known methods for interconversion of ergot cyclic peptide alkaloids.

Conveniently the thia ergot cyclic peptide alkaloid is alkylated and/or hydrogenated to produce an alkylated and/or hydrogenated thia ergot cyclic peptide alkaloid.

For example the compounds may be alkylated in position 1 or 2 of the ergoline nucleus using appropriate selective alkylation methods.

If desired any 9,10 double bond in the ergoline nucleus may be saturated e.g. by catalytic hydrogenation to give the corresponding 9,10-dihydro-9'-thia ergot cyclic peptide alkaloids.

The compounds of the invention may be isolated and purified in conventional manner. The compounds of the invention may be produced as a mixture of the 8R and 8S isomers especially when a double bond is present in the 9,10 position. These may be separated by chromatography. If desired the 8R and 8S isomers may be epimerized in known manner, e.g. by treatment with acids.

Free base forms of the compounds of the invention may be converted into acid addition salt forms in conventional manner and vice versa. Suitable acids for salt formation include hydrochloric acid, sulphuric acid, maleic acid, fumaric acid, tartaric acid and methanesulphonic acid.

Insofar as the production of any particular starting material is not particularly described, the compound is known or may be made in conventional manner.

In the following examples all temperatures are in degrees Centigrade and are uncorrected.

EXAMPLE 1: [Process a]

9,10-dihydro-9'-thia-α-ergocryptine or N-([2R,5S,10aS,10bS]-hexahydro-10b-hydroxy-5-isobutyl-2-isopropyl-3,6-dioxo-8H,10H-oxazolo[3,2-a]thiazolo[4,3-c]pyrazin-2-yl)-6-methyl-5R-(8β)ergoline-8-carboxamide 30 ml of absolute dimethylformamide are cooled with stirring to −15° and a solution of 1 ml oxalyl chloride in 5 ml absolute acetonitrile is added dropwise thereto. 2.95 g dry 9,10-dihydrolysergic acid are added and a grey-white precipitate is formed. The mixture is stirred for 30 minutes, treated at 0° with 6 ml absolute pyridine with vigorous cooling, and then with 1.40 g (2R,5S,10aS,10bS)-2-amino-dihydro-10b-hydroxy-5-isobutyl-2-isopropyl-8H,10H-oxazolo[3,2-a]thiazolo[4,3-c]pyrazin-3(2H),6(5H)dione hydrochloride, and then stirred vigorously for 2 hours. The temperature of the mixture is allowed to rise slowly from −10° to 0°.

To work up, 6.5 ml citrate buffer (pH 4) is added to the mixture with strong cooling. The mixture is made alkaline with 2N sodium carbonate solution, and extracted thrice with methylene chloride. The combined extracts are dried over sodium sulphate, filtered and concentrated. The concentrate is chromatographed on 100 g silicagel to afford on elution with 3% methanol in methylene chloride, the title compound which is crystallized from methylene chloride/ether.

M.pt.: 182°–184° (decomp); $[\alpha]_D^{20} = +9.6°$ (c=0.5 in dimethylformamide).

The amino cyclol is obtained as follows:

(a) (6S,8aS)-dihydro-6-isobutyl-3H-thiazolo[3,4-a]-pyrazin-5(6H),8(7H)-dione 61 g L-thiazolidine-4-carboxylic acid methyl ester in 450 ml absolute ether are added to a solution of 95.8 g N-tert-butyloxycarbonyl-L-leucine in 450 ml absolute ether. The mixture is stirred for 15 minutes at room temperature. A solution of 94.4 g dicyclohexylcarbodiimide in 200 ml absolute ether is added dropwise and after being stirred for 90 minutes the mixture is filtered to remove the urea. The filtrate is extracted in turn with 1N hydrochloric acid, ice water, 2N sodium bicarbonate solution and ice water.

The aqueous phases are back-extracted with ether. The organic phases are combined, dried with sodium sulphate, filtered and concentrated. The resultant residue is reacted further as such.

The so-obtained protected dipeptide is dissolved in 350 ml absolute methylene chloride and the solution is treated with 140 ml trifluoroacetic acid with ice cooling. The mixture is maintained standing at room temperature for 16 hours and then concentrated in a rotary evaporator. The residue is taken up in methylene chloride and made alkaline with 2N sodium carbonate solution. The mixture is twice extracted back with methylene chloride. The combined organic phases are concentrated, dried over sodium sulphate, filtered and concentrated. The heading compound crystallized after taking up in ether and adding hexane.

M.pt. 142°–143°; $[\alpha]_D^{20} = 113°$ (c=0.8 in chloroform).

(b) (2R,5S,10aS,10bS)-Hexahydro-10b-hydroxy-5-isobutyl-2-isopropyl-3,6-dioxo-8H,10H-oxazolo[3,2-a]thiazolo[4,3-c]pyrazine-2-carboxylic acid ethyl ester 72.7 g (6S,8aS)-Dihydro-6-isobutyl-3H-thiazolo[3,4-a]pyrazin-5(6H),8(7H)-dione in 175 ml absolute dioxane are treated with 114.5 g S(+)-isopropyl-benzyloxy malonic acid mono ethyl ester acid chloride and 50.9 g 2,6-lutidine. The mixture is stirred for 4 hours at 70°, diluted with 1 liter ether and treated twice with in turn 2N hydrochloric acid and saturated sodium bicarbonate solution. The aqueous phases are back-extracted twice with ether. The combined ether phases are dried over sodium sulphate, filtered and concentrated in a vacuum. The brown residue is chromatographed on 2.4 kg silicagel to afford, on elution with 2% methanol in methylene chloride, the resultant acyl derivative which is further reacted as such after concentration to give a yellow oil.

The resultant acyl derivative is dissolved in 600 ml trifluoroacetic acid. The mixture is allowed to stand for 18 hours at room temperature.

The resultant red-brown solution is concentrated. The residue is taken up in 1 liter methylene chloride and made alkaline with 2N sodium carbonate solution. The aqueous phase is separated off and back-extracted twice with 300 ml methylene chloride. The combined organic phases are dried over sodium sulphate, filtered and concentrated in a vacuum. The red brown crude product is chromatographed on 2.4 kg silicagel to give on elution with 2% methanol in methylene chloride the heading compound which is crystallized from ether/petroleum ether to give white crystals.

M.pt. 106°–108°; $[\alpha]_D^{20} = -7.5°$ (c=1.0 in chloroform).

(c) (2R,5S,10aS,10bS)-Hexahydro-10b-hydroxy-5-isobutyl-2-isopropyl-3,6-dioxo-8H,10H-oxazolo[3,4-a]thiazolo[4,3-c]pyrazine-2-carboxylic acid 27.6 g (2R,5S,10aS,10bS)-Hexahydro-10b-hydroxy-5-isobutyl-2-isopropyl-3,6-dioxo-8H,10H-oxazolo[3,2-a]thiazolo[4,3-c]pyrazine-2-carboxylic acid ethyl ester are dissolved in 600 ml 1N sodium hydroxide solution and stirred for 5 hours at room temperature. To work up the mixture is adjusted to pH 4.5 with 2N hydrochloric acid and repeatedly extracted with ethyl acetate. The organic extracts are dried, and concentrated at under 30° to remove the solvent. The heading compound is obtained as white crystals on dilution with ether.

M.pt. 149°–151° (decomp).

(d) (2R,5S,10aS,10bS)-Hexahydro-10b-hydroxy-5-isobutyl-2-isopropyl-3,6-dioxo-8H,10H-oxazolo[3,2-a]thiazolo[4,3-c]pyrazine-2-carbonyl-azide A solution of 6 ml oxalyl chloride in 50 ml absolute methylene chloride is added dropwise within 10 minutes to a stirred mixture of 7 ml absolute dimethylformamide and 100 ml absolute methylene chloride cooled to −15°. The mixture is stirred for a further 10 minutes, and diluted with 100 ml absolute ether. 17.3 g (2R,5S,10aS,10bS)-Hexahydro-10b-hydroxy-5-isobutyl-2-isopropyl-3,6-dioxo-8H,10H-oxazolo[3,4-a]thiazolo[4,3-c]pyrazin-2-carboxylic acid are quickly added. A clear solution results which is stirred for 10 minutes at −10°. A solution of 30 g sodium azide in 120 ml water is added. The mixture is treated with 800 ml methylene chloride and the resultant two phase mixture is vigorously shaken for 4 minutes. 1 liter ice cold saturated sodium bicarbonate solution is added. The organic phase is separated off and dried over sodium sulphate. The solvent is removed by concentrating the mixture to give a residue which on treatment with absolute ether yields heading compound as white crystals.

M.pt. 100° (Fulmination).

(e) (2R,5S,10aS,10bS)-2-Amino-dihydro-10b-hydroxy-5-isobutyl-2-isopropyl-8H,10H-oxazolo[3,2-a]thiazolo[4,3-c]pyrazin-3(2H),6(5H)-dione A solution of 12.7 g (2R,5S,10aS,10bS)-hexahydro-10b-hydroxy-5-isobutyl-2-isopropyl-3,6-dioxo-8H,10H-oxazolo[3,2-a]thiazolo[4,3-c]pyrazine-2-carbonyl azide in 180 ml absolute methyl ethyl ketone is treated with 3.18 ml 10N hydrochloric acid solution and boiled under reflux for 15 minutes. The resultant mixture is concentrated, and diluted with absolute ether to give the heading compound in hydrochloride salt form as yellow crystals.

M.pt. 123°–126° (decomp).

EXAMPLE 2: (Process a)

9′-Thia-α-ergocryptinine and 9′-Thia-α-ergocryptine also known as

N-([2R,5S,10aS,10bS]-Hexahydro-10b-hydroxy-5-isobutyl-2-isopropyl-3,6-dioxo-8H,10H-oxazolo[3,2-a]thiazolo[4,3-c]pyrazin-2-yl)9,10-didehydro-6-methyl-5R-(8α)ergoline-8-carboxamide and N-([2R,5S,10aS,10bS]-Hexahydro-10b-hydroxy-5--isobutyl-2-isopropyl-3,6-dioxo-8H,10H-oxazolo[3,2-a]thiazolo(4,3-c]pyrazin-2-yl)9,10-didehydro-6-methyl-5R-(8β)ergoline-8-carboxamide.

2.5 g anhydrous lysergic acid in 25 ml absolute dimethylformamide are dissolved through the addition of 2.11 g trifluoroacetic acid. The mixture is stirred and cooled to −10° and at this temperature a mixture of 2.52 g trifluoroacetic acid anhydride in 15 ml absolute acetonitrile is added dropwise within 5 minutes. The clear solution is stirred for 10 minutes. Then under vigorous cooling 15 ml pyridine and 2.71 g (2R,5S,10aS,10bS)-2-amino-dihydro-10b-hydroxy-5-isobutyl-2-isopropyl-8H,10H-oxazolo[3,2-a]thiazolo[4,3-c]pyrazin-3(2H),6(5H)-dione hydrochloride are added. The reaction mixture is stirred for a further 1 hour from −10° to 0°.

To work up 200 ml methylene chloride are added and the mixture is well shaken with 100 ml 2N sodium carbonate solution. The aqueous phase is separated off and is back extracted twice with 100 ml methylene chloride each time. The combined aqueous phases are dried over sodium sulphate and concentrated in a vacuum. The residue is chromatographed on 250 g silicagel to elute with 2% methanol in methylene chloride 9′-thia-α-ergocryptinine which is recrystallized from methanol, M.pt. 228°–230° (decomp); $[\alpha]_D^{20} = +281°$ (c=0.8 in dimethylformamide), and with 3% methanol in methylene chloride first fractions containing mixtures of ergot alkaloids and then pure 9′-thia-α-ergocryptine which is crystallized from ether.

M.pt. 203°–205° (decomp); $[\alpha]_D^{20} = +46°$ (c=0.7 in dimethylformamide).

EXAMPLE 3: (process b)

9′-thia-ergotamine and 9′-thia-ergotaminine

1. Cultivation of strain NRRL 12043
(a) Pre-culture

About $10^9$ conidia of a slant culture of the Claviceps purpurea ergotamine/ergotaminine producing strain NRRL 12043 are suspended in 10 ml sterile water.

200 ml of a preculture medium of the following composition:

| Components | g/liter |
|---|---|
| Saccharose | 100 |
| Proflo* | 10 |
| Ammonium oxalate | 3 |
| Ca (NO$_3$)$_2$.4H$_2$O | 1 |
| KH$_2$PO$_4$ | 0.25 |
| MgSO$_4$.7H$_2$O | 0.25 |
| KCl | 0.125 |
| FeSO$_4$.7H$_2$O | 0.0166 |
| ZnSO$_4$.7H$_2$O | 0.0068 |
| distilled water ad | 1 liter |

*Proflo is a dried and ground cotton flower seed available from Traders Protein U.S.A. having on analysis 60% protein, 4% fat, 22% sugar, 6% ash, 2% moisture and 6% fibre.

in a 500 ml Erlenmeyer flask are made up. The pH of the mixture is adjusted to 6.5 with ammonium hydroxide. The medium is sterilized at 120° C. for 20 minutes. The medium is inoculated with the conidia. The pre-culture is shaken at 24° on a rotary shaker for 5 days (180 rpm and 5 cm shaking circle). At the end of the growth the culture has a pH of 5.3 and a dry mycelial mass of the pre-culture of about 22 g/liter.

(b) Fermentation culture 10 ml of the pre-culture is used to inoculate 50 ml of a main culture medium of the following composition:

| Components | g/liter |
| --- | --- |
| Saccharose | 240 |
| Ammonium oxalate | 9.6 |
| Ca (NO$_3$)$_2$.4H$_2$O | 2.5 |
| MgSO$_4$.7H$_2$O | 0.625 |
| KH$_2$PO$_4$ | 0.625 |
| KCl | 0.312 |
| FeSO$_4$.7H$_2$O | 0.0252 |
| ZnSO$_4$.7H$_2$O | 0.0102 |
| distilled water ad | 1 liter | in a 500 ml Erlenmeyer flask. The pH has been adjusted with 25% ammonium hydroxide to 6.2. The medium is sterilized at 110° for 20 minutes.

The culture is incubated at 24° in a rotary shaker (180 rpm, 5 cm shaking circle). After 4 days cultivation time each culture is treated with 90 mg L-thiazolidine-4-carboxylic acid. The cultures are incubated for a further 10 days in the rotary shaker. After the fermentation has finished the cultures are filtered. The mycelium is dried carefully. The dry mycelial mass of the main culture is about 85 g/liter. The total alkaloid content is about 12 mg/g, and the weight of 9'-thiaergotamine and 9'-thiaergotaminine is about 10% of the total alkaloid content.

2. Isolation of 9'-thiaergotamine and 9'-thiaergotaminine 500 g dry mycelium is twice homogenized each time with 1600 ml methanol and 2% concentrated ammonium hydroxide and further twice homogenized each time with 1200 ml methanol, each homogenization taking 5 minutes in an ultrasonic homogenizer such as an Ultra Turrax apparatus. The combined filtrates are concentrated in a vacuum at a maximum of 40° bath temperature to give about 50 g wine-red residue. The residue is dissolved in 500 ml methanol and filtered through a chromatograph tube of 10 cm diameter and containing 500 g aluminium oxide of Activity II (Woehlm), which is washed with 2000 ml methanol. The combined filtrates are evaporated to dryness in a vacuum to give 25 g yellow foam. The residue is chromatographed on a 200 fold silicagel (Brand 60 Merck) using 2% methanol in methylene chloride and the fractions are examined by thin layer chromatography and those fractions which have only spots corresponding to 9'-thia ergot alkaloids are further purified (see table I).

Table I below gives representative Rf values for ergotamine (Et) and ergotaminine (Et-in) and the corresponding thia derivatives in different thin layer chromatographic systems.

TABLE I

| | Rf values | | | |
| --- | --- | --- | --- | --- |
| Layer and solvent | Thia-Et | Et | Thia-Et-in | Et-in |
| Aluminium oxide[1] | | | | |
| Ethylacetate/sec. Butanol | 0.44 | 0.34 | 0.68 | 0.59 |
| 9:1 | | | | |
| Toluene/iso-Propanol 9:1 | 0.58 | 0.50 | 0.69 | 0.63 |
| Toluene/iso-Propanol 19:1 | 0.30 | 0.24 | 0.58 | 0.46 |
| Silicagel[2] | | | | |
| Toluene/iso-Propanol 85:15 | 0.15 | 0.11 | 0.43 | 0.31 |
| CH$_2$Cl$_2$/MeOH 93:7 | 0.25 | 0.22 | 0.65 | 0.52 |

[1]Aluminium oxide plates Merck F 254 (Type E)
[2]Silicagel plates Merck F 254

On the thin layer chromatographic plates the substance spots appear under UV light (254 nm) as blue-violet and (366 nm) as bright blue spots. They can also be detected with iodine vapour as brown spots.

The van Urk reagent can also be used to detect the substance, which appears blue-violet, which is made more intensive in daylight or by treatment with nitric dioxide.

9'-thiaergotamine

The appropriate chromatography fractions containing only 9-thiaergotamine are concentrated, dissolved in ethyl acetate, filtered through talc, and after concentration in a vacuum treated with a little hexane whereupon the alkaloid crystallises out. The crystals are recrystallized from the same system to give white to yellowish crystals.

M.pt. from 199° (slow decomp) $[\alpha]_D^{20} = -165°$ (c=0.5 in chloroform)

mesylate m.pt. 211° (decomp); $[\alpha]_D^{20} = +76°$ (c=0.51 in methanol).

9'-thiaergotaminine

In analogous manner to the isolation of 9'-thiaergotamine, the appropriate fractions containing 9'-thiaergotaminine are purified to give white crystals.

M.pt. from 199° (decomp); $[\alpha]_D^{20} = +343°$ (c=0.55 in chloroform).

EXAMPLE 4: (process b)

9'-thiaergocristine and 9'-thiaergocristinine

1. Cultivation of strain NRRL 12044

The ergocristine/ergocristinine producing Claviceps purpurea strain NRRL 12044 is cultivated in analogous manner to that described in Example 3. The dry mycelium mass of the main culture is about 80 g/liter and the alkaloid content is about 10 mg/g. The title compounds comprise about 8% of the total alkaloid content.

2. Isolation of 9'-thiaergocristine and 9'-thiaergocristinine 500 g dry mycelia are twice homogenized each time with 1500 ml methanol and 2% concentrated ammonium hydroxide and further twice homogenized with 1200 ml ethanol, each homogenization taking 5 minutes in a ultra-sonic homogenizer such as an Ultra Turrax apparatus. The combined filtrates are concentrated in a vacuum at a maximum 40° bath temperature to give about 190 g wine-red residue. The residue is dissolved in 900 ml methanol and filtered through a 10 cm high layer of 600 g aluminium oxide (basic, activity II) which is washed with 2000 ml methanol. The combined filtrates are concentrated to dryness in a vacuum to give a residue of about 108 g. The residue in methanol is chromatographed on 3000 g Sephadex cellulose derivative LH-20 and 200 ml fractions collected and concentrated. The fractions containing the title thia ergot alkaloids are purified (ca 526 mg dry weight) the Rf values being given in Table II in comparison to ergocristine [Ec] and ergocristinine [Ec-in].

TABLE II

| | Rf values | | | |
|---|---|---|---|---|
| Layer and solvent | Thia-Ec | Ec | Thia-Ec-in | Ec-in |
| Aluminium oxide[1] | | | | |
| Ethylacetate/sec. Butanol 9:1 | 0.68 | 0.63 | 0.78 | 0.70 |
| Toluene/iso-Propanol 9:1 | 0.68 | 0.62 | 0.69 | 0.66 |
| Toluene/iso-Propanol 19:1 | 0.50 | 0.42 | 0.58 | 0.47 |
| Silicagel[2] | | | | |
| Toluene/iso-Propanol 85:15 | 0.37 | 0.28 | 0.56 | 0.48 |
| $CH_2Cl_2$/MeOH 93:7 | 0.47 | 0.41 | 0.70 | 0.60 |

[1] and [2] See Table I. For detection see example 3.

The fractions containing the thia title compounds are chromatographed on Sephadex LH-20 (120 g) in methanol to give 156 mg of a mixture of the pure title compounds which are separated by silicagel chromatography (Merck 60) using 2% methanol in methylene chloride as eluant.

9'-thiaergocristine (recrystallized from benzene) m.pt. 146° (sintering with slow decomp); $[\alpha]_D^{20} = -176°$; (c=0.5 in chloroform).

9'-thiaergocristinine (recrystallized from ethanol-/ethyl acetate). m.pt. 209°-210°; (decomp); $[\alpha]_D^{20} = +344°$ (c=0.51 in chloroform).

EXAMPLE 5

The title compounds of Example 2 may be produced in analogous manner to that described in Example 3 or 4 using an ergocryptine/ergocryptinine-producing strain.

The title compounds of Example 3 and 4 may be produced in analogous manner to that described in Example 1. from the corresponding aminocyclol of formula II wherein either $R_1$ is methyl and $R_2$ is benzyl or $R_1$ is isopropyl and $R_2$ is benzyl.

In analogous manner to that disclosed in Example 1 the following compounds may be produced:

(a) 2-methyl-9,10-dihydro-9'-thia-α-ergocryptine. m.pt. 176°-180° (decomp); $[\alpha]_D^{20} = -1.25°$ (c=0.6 in dimethylformamide).

(b) 6-nor-6-ethyl-9,10-dihydro-9'-thia-α-ergocryptine. m.pt. 212°-214° (decomp); $[\alpha]_D^{20} = +7.9°$ (c=0.5 in dimethylformamide).

(c) 9,10-dihydro-9'-thia-ergotamine. m.pt. 235°-237°; $[\alpha]_D^{20} = -23.6°$ (c=0.5 in dimethylformamide).

In analogous manner to that described in Example 2 the following compounds are produced:

(d) 2-bromo-9'-thia-α-ergocryptine. M.p. 170°-173° (decomp) Optical Rotation D line 20° C.= +16.4 (c=0.7 in dimethylformamide).

(e) 2-bromo-9'-thia-α-ergocryptinine. M.p. 193°-200° (decomp). Optical rotation at D line= +355° (c=0.5 in dimethylformamide).

The compounds of the invention have not been described in the literature.

The compounds of the invention are useful because they possess pharmacological activity in animals. In particular, the compounds of the invention exhibit dopaminergic stimulant activity, as indicated by standard animal tests.

In one test carried out according to the principles of U.Ungerstedt,Acta.physiol.Scand.Suppl.No.367, 1971,p. 69–93, 6-hydroxydopamine is injected into rats to provoke unilateral degeneration of the nigro-neostriatal dopamine system and on injection p.o. of about 0.05 to about 100 mg/kg (e.g. 30 to 100 mg/kg) of the compounds, the rats turn contra-laterally.

The compounds moreover induce stereotypy in the rat at a dose of about 30 mg/kg i.p.

The compounds are therefore useful in the treatment of Morbus Parkinson.

For the above mentioned use the dosage will, of course, vary depending on the compound employed, mode of administration and therapy desired. However, in general, satisfactory results are obtained when administered at a daily dosage of from 0.005 mg to about 100 mg per kg animal body weight, conveniently given in divided doses 2 to 4 times a day or in sustained release form. For the larger mammal, the total daily dosage is in the range from about 0.1 to about 100 mg, e.g. 0.1 to 20 mg or 1 to 100 mg, and dosage forms suitable for oral administration comprise from about 0.02 mg to about 50 mg of the compounds admixed with a solid or liquid pharmaceutical carrier or diluent.

Additionally, the compounds of the invention exhibit prolactin secretion inhibitory activity, as indicated by in standard tests. For example in one test effected according to the principles of Experientia 34, 1978, p.1330 the compounds inhibit implantation in rats at a dose of from about 0.01 to about 1 mg/kg s.c. and inhibit lactation in rats at a dose of from about 1 to about 10 mg/kg p.o.

The compounds are therefore useful as prolactin secretion inhibitors, e.g. for the prevention or suppression of physiological lactation and to treat prolactin-induced pathological states, such as the treatment of acromegaly.

For this use the dosage will, of course, vary depending on the compound employed, mode of administration and therapy desired. However, in general, satisfactory results are obtained when administered at a daily dosage of from 0.01 mg to about 10 mg per kg animal body weight, conveniently given in divided doses 2 to 4 times a day or in sustained release form. For the larger mammal, the total daily dosage is in the range from about 5 to about 100 mg, and dosage forms suitable for oral administration comprise from about 1 mg to about 50 mg of the compounds admixed with a solid or liquid pharmaceutical carrier or diluent.

Furthermore, the compounds exhibit anti-depressant activity, as indicated by their activity in the Ungerstedt test mentioned above and by a serotonergic effect in the sleep/wake test in the chronically implanted rat at doses of from about 3 to about 10 mg/kg p.o. wherein a reduction of the paradoxical sleep phase and an increase in the wake phase is observed [for method see J. M. Vigouret et al. Pharmacology, 1978,16, (1), 156–173].

The compounds are therefore useful as anti-depressant agents, particularly for old subjects.

For this use the dosage will, of course, vary depending on the compound employed, mode of administration and therapy desired. However, in general, satisfactory results are obtained when administered at a daily dosage of from 0.1 mg to about 100 mg per kg animal body weight, conveniently given in divided doses 2 to 4 times a day or in sustained release form. For the larger mammal, the total daily dosage is in the range from about 5 to about 100 mg, and dosage forms suitable for oral administration comprise from about 1 mg to about 50 mg of the compounds admixed with a solid or liquid pharmaceutical carrier or diluent.

Furthermore the compounds of the invention exhibit vasoconstricting activity as indicated by standard tests. For example in by activity on the Arteria carotis externa of the dog at a concentration of from about 10 to about 100 nM/liter in accordance with the principles of E.Müller-Schweinitzer, Naunyn-Schmiedeberg's Arch.Pharmacol. 1976, 292, 113–118.

The compounds are therefore useful as vasoconstricting agents, for example for the treatment of migraine.

Furthermore, the compounds of the invention have venotonizing activity, as indicated by standard tests. For example in the pithed rat test effected according to the principles of R. E. Shipley et al, Proc.Soc.exp.Bio.Med. 1947, 64, 453 or as in Brit.J.Pharmac.-Chemother. 1967,30, 78–87, the compounds provoke a pressor effect and a blood pressure rise on administration of from about 5 to about 20 µg/kg i.v. Furthermore, the compounds constrict the capacitance vessels in doses from about 0.5 to about 50 µg/kg in the Mellander Cat test [see for method Angiologica, 1966, 3, 77–99].

The compounds are therefore useful as venotonizing agents e.g. for the treatment of orthostatic hypotension, and in the prophylaxis of thrombosis.

For the vasoconstricting and venotonizing use the dosage will, of course, vary depending on the compound employed, mode of administration and therapy desired. However, in general, satisfactory results are obtained when administered at a daily dosage of from 0.01 mg to about 10 mg per kg animal body weight, conveniently given in divided doses 2 to 4 times a day or in sustained release form. For the larger mammal, the total daily dosage is in the range from about 5 to about 100 mg, and dosage forms suitable for oral administration comprise from about 1 mg to about 50 mg of the compounds admixed with a solid or liquid pharmaceutical carrier or diluent.

Further the compounds exhibit a vigilance-increasing activity as indicated in standard tests for example in the sleep/wake test in the rat as described above.

Moreover the compounds increase the local cerebral glucose utilisation in the sensomotor cortex, e.g. Hippocampus, Nucleus habenula, Nucleus corpus gentcul. As indicated by the carbon-14-2-deoxyglucose autoradiographic technique with the rat brain on administration i.p. of from about 0.3 to about 30 mg/kg of the compounds [for method see e.g. L. Solokoff, Journal of Cerebral Blood Flow and Metabolism, 1981, (1), 7–36, H. E. Savaki et al. Brain Research 1982, 233, 347 and J. McCulloch et al. Journal of Cerebral Blood Flow and Metabolism 1981, 1, 133–136].

The compounds are therefore useful in the treatment of cerebral insufficiency and senile dementia particularly the early stages thereof.

For this use the dosage will, of course, vary depending on the compound employed, mode of administration and treatment desired. However, in general, satisfactory results are obtained when administered at a daily dosage of from about 0.01 mg to about 100 mg per kg animal body weight, conveniently given in divided doses 2 to 4 times a day or in sustained release form. For the larger mammal, the total daily dosage is in the range of from about 1 to about 100 e.g. 1 to 5, mg and dosage forms suitable for oral administration comprise from about 0.2 mg to about 50 mg of the compounds admixed with a solid or liquid pharmaceutical carrier or diluent.

The present invention also provides compounds of the invention for use as dopaminergic stimulants, prolactin secretion inhibitors, anti-depressants, vasoconstricting and venotonizing agents, and vigilance increasing agents and for example for the indications defined above.

The 9,10-dihydro-9'-thia-α-ergocryptine and 2-methyl-9,10-dihydro-9'-thia-α-ergocryptine are the preferred compounds. The vigilance increasing activity is the preferred activity.

The compounds of the invention may be administered in the form of a pharmaceutically acceptable acid addition salt. Such salt forms have the same order of activity as the free base forms.

The present invention accordingly provides a compound of the invention in free base form or in pharmaceutically acceptable acid addition salt form in association with a pharmaceutical carrier or diluent. Such compositions may be formulated in conventional manner so as to be, for example, a solution or a tablet.

The compounds of the invention may be used in analogous manner to standard compounds used for the indications mentioned above.

For example the preferred compound 2-methyl-9'-thia-9,10-dihydro-α-ergocryptine exhibits in the carbon-14-2-desoxyglucose autoradiographic test mentioned above at 3 mg/kg i.p. the following increases

|  | % |
|---|---|
| Hippocampus | +2 |
| Nucleus lateralis huberula | +22 |
| Nucleus dors.corpus genicul.lat | +25 | and has a score in the apomorphine stereotypy test of 15.7 at 30 mg/kg i.p.

What we claim is:
1. A compound of formula I

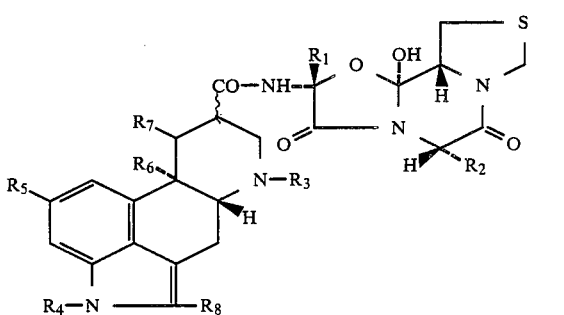

wherein
R$_1$ is (C$_{1-4}$)alkyl,
R$_2$ is (C$_{1-6}$)alkyl or benzyl,
R$_3$ and R$_4$ independently are hydrogen or (C$_{1-4}$)alkyl,
R$_5$ is hydrogen or bromine,
R$_6$ and R$_7$ are each hydrogen, or
R$_6$ and R$_7$ together form a single bond, or
R$_6$ is methoxy and R$_7$ is hydrogen, and
R$_8$ is hydrogen, methyl, or halogen of atomic number from 9 to 35, with the proviso that when $R_5$ is bromine $R_7$ is hydrogen, in free base form or in pharmaceutically acceptable acid addition salt form.

2. A compound according to claim 1 of formula I

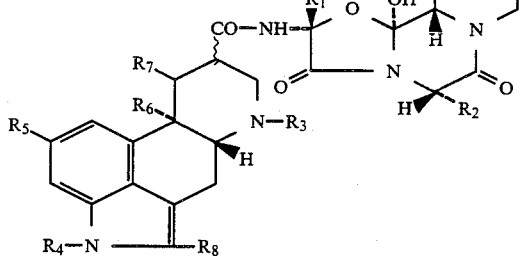

wherein $R_1$ is methyl or isopropyl;

$R_2$ is n-propyl, isopropyl, n-butyl, isobutyl, sec-butyl or benzyl;

$R_3$ is methyl, ethyl, n-propyl or isopropyl;

$R_4$ is hydrogen or methyl;

$R_5$ is hydrogen;

$R_6$ and $R_7$ are each hydrogen or together form a single bond; and $R_8$ is hydrogen, methyl or bromine, in free base form or pharmaceutically acceptable acid addition form.

3. A compound according to claim 2 in which $R_1$ is methyl or isopropyl, $R_2$ is isobutyl or benzyl, $R_3$ is methyl or ethyl, $R_4$ is hydrogen or methyl, and $R_5$, $R_6$, $R_7$ and $R_8$ are each hydrogen.

4. A compound of claim 1 of formula Ia wherein $R_1{}^I$ is methyl and $R_2{}^I$ is isobutyl or benzyl, or
$R_1{}^I$ is ethyl and $R_2{}^I$ is benzyl, or
$R_1{}^I$ is isopropyl and $R_2{}^I$ is isopropyl, sec-butyl, isobutyl or benzyl, in free base form or in pharmaceutically acceptable acid addition salt form.

5. The compound of claim 1 which is 2-methyl-9,10-dihydro-9′-thia-α-ergocryptine in free base form or in pharmaceutically acceptable acid addition salt form.

6. The compound according to claim 1 which is 9,10-dihydro-9′-thia-α-ergocryptine in free base form or pharmaceutically acceptable acid addition form.

7. The compound according to claim 1 which is 9′-thia-α-ergocryptinine in free base form or pharmaceutically acceptable acid addition form.

8. The compound according to claim 1 which is 9′-thia-α-ergocryptine in free base form or pharmaceutically acceptable acid addition form.

9. The compound according to claim 1 which is 9′-thia-ergotamine in free base form or pharmaceutically acceptable acid addition form.

10. The compound according to claim 1 which is 9′-thia-ergotaminine in free base form or pharmaceutically acceptable acid addition form.

11. The compound according to claim 1 which is 9′-thiaergocristine in free base form or pharmaceutically acceptable acid addition form.

12. The compound according to claim 1 which is 9′-thiaergocristinine in free base form or pharmaceutically acceptable acid addition form.

13. The compound according to claim 1 which is 6-nor-6-ethyl-9,10-dihydro-9′-thia-α-ergocryptine in free base form or pharmaceutically acceptable acid addition form.

14. The compound according to claim 1 which is 9,10-dihydro-9′-thia-ergotamine in free base form or pharmaceutically acceptable acid addition form.

15. A pharmaceutical composition comprising a compound of claim 1 in association with a pharmaceutical carrier or diluent.

* * * * *